(12) United States Patent
Kiguchi et al.

(10) Patent No.: US 8,750,951 B2
(45) Date of Patent: Jun. 10, 2014

(54) LIVING BODY OPTICAL MEASUREMENT SYSTEM

(75) Inventors: Masashi Kiguchi, Kawagoe (JP);
Hirokazu Atsumori, Kawagoe (JP);
Tadahiro Horita, Saitama (JP)

(73) Assignee: Hitachi, Ltd., Tokyo (JP)

( * ) Notice: Subject to any disclaimer, the term of this patent is extended or adjusted under 35 U.S.C. 154(b) by 1437 days.

(21) Appl. No.: 12/216,360

(22) Filed: Jul. 2, 2008

(65) Prior Publication Data
US 2009/0015839 A1 Jan. 15, 2009

(30) Foreign Application Priority Data
Jul. 11, 2007 (JP) ................................ 2007-182189

(51) Int. Cl.
*A61B 5/00* (2006.01)
(52) U.S. Cl.
USPC ........... 600/310; 600/322; 600/331; 600/336; 600/340
(58) Field of Classification Search
USPC ......... 600/310, 314–324, 329–331, 336, 340, 600/344
See application file for complete search history.

(56) References Cited

U.S. PATENT DOCUMENTS

| 7,729,732 B2 * | 6/2010 | Ohashi | 600/310 |
| 7,759,622 B2 * | 7/2010 | Nishimura | 250/206 |

FOREIGN PATENT DOCUMENTS

| JP | 57-115232 | 7/1980 |
| JP | 63-260532 | 4/1987 |
| JP | 63-275323 | 5/1987 |
| JP | 04-166144 | 10/1990 |
| JP | 05-317295 | 5/1992 |
| JP | 2001-337033 | 5/2000 |
| JP | 2002-248104 | 2/2001 |
| JP | 2004-333344 | 5/2003 |
| JP | 2006-218013 | 2/2005 |
| JP | 2006-230657 | 2/2005 |

* cited by examiner

*Primary Examiner* — Sean Dougherty
*Assistant Examiner* — Devin Henson
(74) *Attorney, Agent, or Firm* — Stites & Harbison, PLLC; Nicholas B. Trenkle

(57) ABSTRACT

To make the peak value of the driving current of light source smaller than the conventional one and to make the peak value of the light receiving level of light-sensitive elements smaller than the conventional one in order to save power consumption of the device and to improve the precision of measurement, codes of which the bits of the Hadamard codes are shifted by the same bit for each code series having the same bit cycle, or codes of which the bits of a PN code are shifted are used as different codes.

4 Claims, 20 Drawing Sheets

LIVING BODY OPTICAL MEASUREMENT SYSTEM

CLAIM OF PRIORITY

The present application claims priority from Japanese patent application JP 2007-182189 filed on Jul. 11, 2007, the content of which is hereby incorporated by reference into this application.

FIELD OF THE INVENTION

The present invention relates to a living body optical measurement system, or a living body optical measurement system for optically measuring information within a living body.

BACKGROUND OF THE INVENTION

A device for measuring easily the inside of living body without causing damages to the living body is hoped for in such fields as clinical medicine, brain science and the like. For example, when specifically the head is considered as the subject of measurement, brain diseases such as cerebral infarction, brain hemorrhage, etc. and high-order brain functions such as thinking, language, physical exercise and the like are mentioned. And such subjects of measurement are not limited to the head, but also preventive diagnosis relating to heart diseases such as cardiac infarction and the chest region, visceral diseases of the kidney, liver and the like in the abdomen are mentioned. When the head is considered as the subject of measurement and diseases in the brain or high-order brain functions are measured, it is necessary to clearly specify the involved area or the functional region. For this reason, it is very important to measure a wide area of the head as an image.

For the requirements mentioned above, optical measurements are very effective, because the normal and abnormal state of living body organs and the activation of the brain relating to high-order brain functions are closely related with the oxygen metabolism and blood volume within the living body. These oxygen metabolism and blood volume correspond to the density of specific pigments (hemoglobin, cytochrome aa3, myoglobin, etc.) in living body, and this pigment density is calculated by the amount of light absorption in the visual—infrared wavelength range. Devices for measuring the inside of living body by irradiating light in the visually infrared wavelength range on living body and detecting the light reflected by the living body are described for example in JP-A-Sho57 (1982)-115232, JP-A-Sho63 (1988)-260532, JP-A-Sho63 (1988)-275323 and JP-A-Hei5 (1993)-317295.

So far, time-division multiplex modulation system, frequency multiplexing system and the like among light-intensity modulation systems have been used for the measurement of light in living body. The basic structure is that of deriving intensity data by means of optical detection with the help of a lock-in amplifier, and time-division multiplexing or frequency multiplexing has been adopted to increase points of measurement.

On the other hand, an art based on CDMA (code division multiplex access) is described in JP-A-2004-333344. This is constituted by the use of Hadamard codes, the implementation of a CDMA modulation (intensity modulation), and the separation of light source and emission of light on the light receiving side. This art enabled to use the CDMA method for calculating the inside of living body.

SUMMARY OF THE INVENTION

We will describe below the operation of a living body optical measurement device using the conventional CDMA modulation system. FIG. 1 shows the outline of a device using the conventional CDMA modulation system. Light irradiation devices 101, 102, and 103 include respectively a code generating unit 111, 121, and 131, a light modulating unit 112, 122 and 132, a light irradiating unit 113, 123 and 133. The code generating unit 111, 121 and 131 generate respectively circulating code series C1 "1, 0, 1, 0", C2 "1, 0, 1, 0", and C3 "1, 0, 1, 0." The light modulating unit 112, 122, and 132 generates codes subjected to intensity modulation by the code series C1, C2 and C3. The codes subjected to intensity modulation blink the light source elements 114, 124 and 134 of the light irradiating units 113, 123 and 133. The light source lights up when its code series C1, C2 and C3 are in position "1" and goes out when its code series C1, C2 and C3 are in position "0." The light (emitted light) emitted from the light source elements 114, 124 and 134 is irradiated on the subject of irradiation as optical signals at the irradiation positions 115, 125 and 135.

The respective irradiated light reaches the light-sensitive element 117 of the light detecting unit 116 after transmitting/diffusing in the living body which is the subject of irradiation. Here, the optical signal is converted into electrical signal by photoelectric effect. This electrical signal is divided into three signals, and the series C'1, C'2 and C'3 synchronized with the original series are multiplied by three multiplier circuits 118 in the signal processing unit 119. Here, the series C'1, C'2 and C'3 are series generated by the modulation code generating unit 151, 152 and 153. The correlation detecting unit 140 detects the correlation of the respective result of multiplication and outputs the correlation detection outputs which are detection results 141, 142 and 143.

Here, what is used as the CDMA modulation codes is a signal system called Hadamard codes (Walsh-Hadamard codes). This code system is characterized by (1) an outstanding correlatively of being able to completely remove other series of codes which are also Hadamard codes, and (2) an equal number of "1" and "0" constituting the codes resulting in a duty ratio of codes of 50%.

The generating method is as described below:

[Equation 1]

$$H_1 = [1] \tag{1}$$

$$H_{n+1} = \begin{bmatrix} H_n & H_n \\ H_n & -H_n \end{bmatrix} \tag{2}$$

[Equation 2]

$$H_2 = \begin{bmatrix} 1 & 1 \\ 1 & 0 \end{bmatrix} \tag{3}$$

$$H_3 = \begin{bmatrix} 1 & 1 & 1 & 1 \\ 1 & 0 & 1 & 0 \\ 1 & 1 & 0 & 0 \\ 1 & 0 & 0 & 1 \end{bmatrix} \tag{4}$$

Assuming that $H_1=[1]$, then $-H_1=[0]$. The recursive substitution of this leads to the formation of a Hadamard matrix and Hadamard codes. As a result, as $H_2$ and $H_3$, a Hadamard matrix (Hadamard codes) expressed in the following determinant of matrix can be obtained.

We will then describe in details the process of modulation and separation/demodulation of codes. FIG. 2 shows the signals that enter light sensitive elements. At this time, the light sensitive elements receive the input of three lights in a mixed form by the addition effect 201. The difference of amplitude of signals inputted into the light sensitive elements (illustration omitted) depending on the irradiation position 115, 125 and 135 in FIG. 2 is due to the difference of the driving current of the light sensitive elements and the difference of transmission/diffusion characteristics of light between various irradiation positions 115, 125, and 135 and the light sensitive element. And when the transmission characteristic of light is different because of a difference in the wavelength of light irradiated towards the respective irradiation position, a difference in amplitude results likewise. Here, the values in the figure are inputted and outputted by time series from the right.

As shown in FIG. 3, the output of light sensitive elements (light-receiving signal 301) is proportional to the result of addition of input light of FIG. 2. In other words, the codes "6, 3, 1, 2" in time series are outputted in a cyclical form (6, 3, 1, 2, 6, 3, 1, 2, ... ). Since each code has a duty ratio of 50%, the result of addition is 3 in average. If an AC coupling process is carried out in the actual circuit, the light-receiving signal 302 of "3, 0, −2, −1" in time series with the value 3 before the coupling as its center are outputted in a cyclical form.

We will describe the method of detecting signals from the irradiation position 115. As shown in FIG. 4, the AC-coupled light-receiving signals 302, in other word "3, 0, −2, −1" is multiplied in a synchronized form by the series C'1. "1, −1. 1. −1" obtained by implementing a conversion defined by the multiplication by 2 of and the subtraction of 1 from each value of the code series C1 "1, 0, 1, 0" used at the time of generating the original code, and then the result is added for each 4 bits, and is outputted as the detection result. In other words, the signals are calculated and processed as follows: 3×1+0×(−1)+(−2)×1+(−1)×(−1)=3+0+(−2)+1=2 and a value of "2" is outputted as the detection result 141. Here, the term "synchronized" means that the correspondence and variation points of a certain value "1" and "0" of the series C1 mentioned above and the value "1" or "−1" by the conversion mentioned above corresponding thereto are the same on the time axis.

Similarly, we will show the calculation/processing process for the signals from the irradiation points 125 and 135 by the conversion series C'2 and C'3 of the series C2 and C3 in FIG. 5 and FIG. 6. By this calculation/processing process, the output of the signal from the irradiation positions 115, 125 and 135 will be respectively 2, 6, 4. These values 141, 142 and 143 are the double values of the signal amplitude "1, 3, 2" from the irradiation positions 115, 125 and 135 shown in FIG. 2. This fact shows that the detection has been correctly carried out.

After the process described above, signals are subjected to a modulation of intensity, optical signals are transmitted and post-photoelectric conversion signals are demodulated by using the CDMA method in the device to measure the activity of the living body serving as the transmission route of light.

When we take a look at signals in the device here, we can consider that cyclical signals of "6, 3, 1, 2" in the time series form described above as optical signals of the light received and as the driving current of light source elements. This is a case where there is a difference in the driving current of various light source elements, and if there is no such difference, the variation of normalized current value will be "3, 1, 1, 1." Actually, however, variation occurs due to fluctuation depending on light source elements, or difference in the output setting or output characteristic for each light source element.

In the case of cyclical signals of "6, 3, 1, 2" in the form of time series mentioned above, the maximum value among the cycle defined by four bits is "6" and the minimum value is "1". And in the case of Hadamard codes defined in Equation (1) or Equation (2), any extension of the code length to accommodate to an increased number of light sources results in a larger value of "6" at the top of the cyclical series, and "3" in the case of a normalized value. This leads to an increase in the driving current of light source elements, and to an aggrandizement of the power unit of the device, which constitutes a factor of impediment to the miniaturization of device and to making devices portable being driven by battery.

Then, when signals are considered from the viewpoint of light-sensitive elements in the same way, the level of light received changes by "6, 3, 1, 2" in the form of time series even during the process described above. As a result, the processing unit for demodulating CDMA must receive light, carry out photoelectric conversion and process signals of the maximum level "6" at a level that avoids their saturation. This point increases in the same way as the driving current mentioned above as the number of light sources, in other words, measuring points and irradiation positions increases. This makes light-sensitive elements easily liable to saturate, and reduces the amplification ratio of the amplifier mounted on the processing unit, and as a result causes the dynamic range of measurement to become narrower. In short, this causes a decline in the precision of measurement of the device.

The present invention reduces the peak value of the driving current of light-sensitive elements and light receiving signals by changing the position of two or more signals on the time axis in the living body optical measurement system using the CDMA codes.

Specifically, codes of which bits are shifted by the same bit for each code series having the same bit cycle as Hadamard code, or codes of which bits are shifted by a PN code are used as different codes.

According to the present invention, it is possible to make the peak value smaller than the conventional one by smoothing the driving current of light-sensitive elements in the living body optical measuring system using the CDMA codes, and to make the peak value of light receiving level of light-sensitive elements smaller than the conventional ones.

In this way, it is possible to save power consumption of the living body optical measurement system and to improve the precision of measurement.

DETAILED DESCRIPTION OF THE PREFERRED EMBODIMENTS

We will describe below the preferred embodiments of the present invention.

First Embodiment

Now, we will represent any arbitrary nth bit of an arbitrary Hadamard code series $C(k)$ by $b_n$ or $b(n)$. Furthermore, when the $C(k)$ described above falls periodically under the same code in relation to natural numbers $n1$ and $n2$, we will represent the minimum of these cycles by a bit cycle $a$ of $C(k)$. In other words, the bit cycle $a$ is the minimum value of natural number for which the following equation (5) is valid for an arbitrary $n1$ or $n2$.

$$b(n1 \times a + n2) = b(n2) \quad (5)$$

Here, we will show the series C1, C2 and C3 used in the description of the CDMA system described above in FIG. 1.

TABLE 1

| | Time | | | |
|---|---|---|---|---|
| | 0-t1 | t1-t2 | t2-t3 | t3-t4 |
| | | bit | | |
| Series | b(1) | b(2) | b(3) | b(4) |
| C1 | 1 | 0 | 1 | 0 |
| C2 | 1 | 1 | 0 | 0 |
| C3 | 1 | 0 | 0 | 1 |
| Total | 3 | 1 | 1 | 1 |

Series C1 of Table 1 corresponds to bit cycle 2 and series C2 and series C3 correspond to bit cycle 4. In Hadamard codes, depending on the process of calculation, there are $a/2$ kinds of series for series of the same bit cycle in the case of series of the bit cycle $a$. Here, the series of the same bit cycle is considered as a bit cycle group, and we will call them bit cycle $a$ group. For example, series C2 and series C3 correspond to the bit cycle 4 and are represented by the bit cycle 4 group. Inversely, the bit cycle 4 group represents series C2 and series C3.

Figure 1:
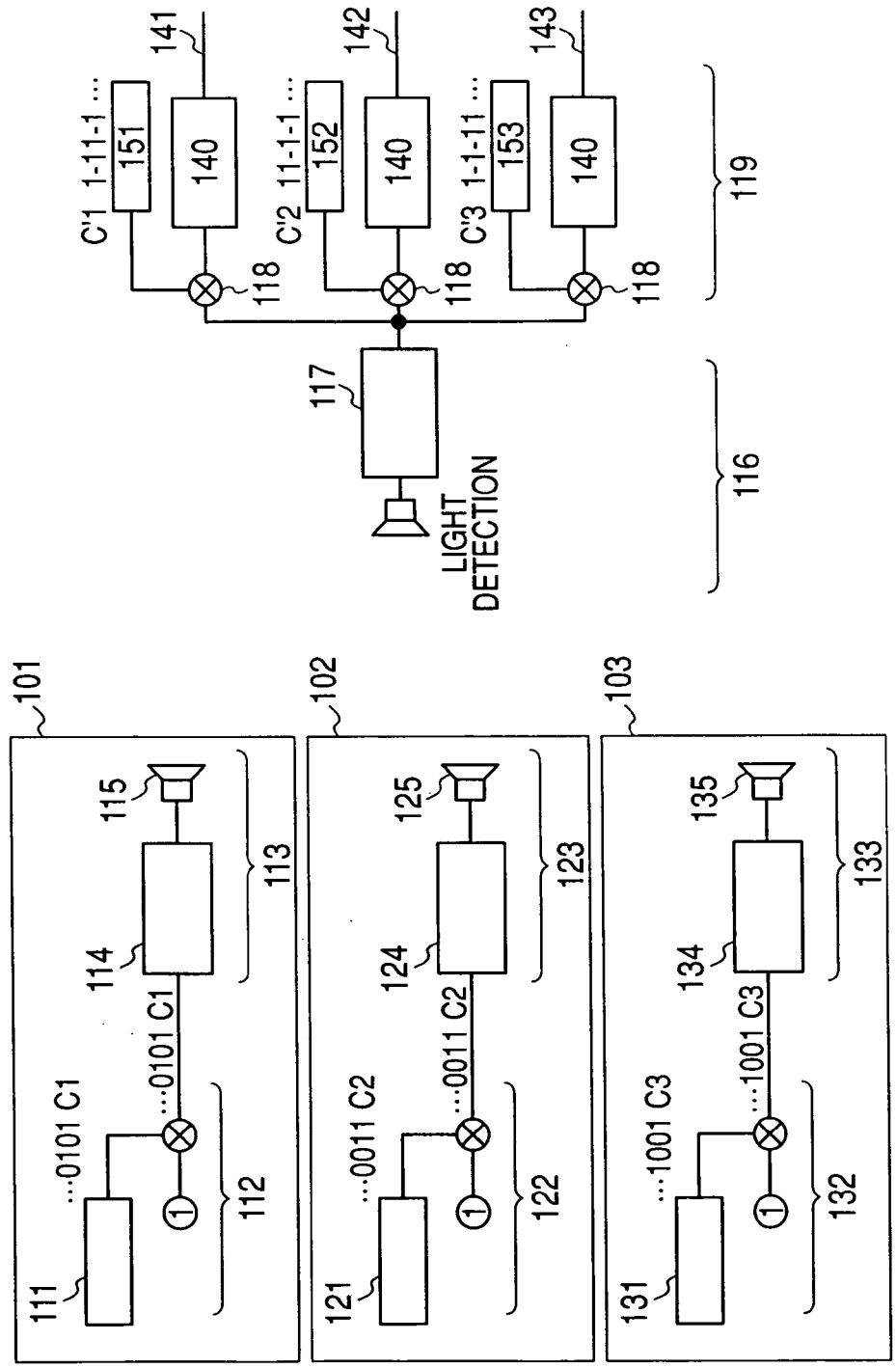
FIG. 1 is a schematic illustration of the CDMA system according to the prior inventions.

We will show in Table 1 the bit bn for each series of code shown in FIG. 1. The bit bn is a binary data constituted by "1" or "0", and according to the configuration shown in FIG. 1, in the case of "1" the light-sensitive elements light up and in the case of "0" they go out. The total shows the number of light-sensitive elements that light up at the time at which each bit bn corresponds.

Here, based on C1, C2 and C3, we generated series C"1, C"2, and C"3 shifted by the bit group described above. We will show them in Table 2.

TABLE 2

| | Time | | | |
|---|---|---|---|---|
| | 0-t1 | t1-t2 | t2-t3 | t3-t4 |
| | | bit | | |
| Series | b"(1) | b"(2) | b"(3) | b"(4) |
| C"1 | 0 | 1 | 0 | 1 |
| C"2 | 0 | 0 | 1 | 1 |
| C"3 | 0 | 1 | 1 | 0 |
| Total | 0 | 2 | 2 | 2 |

Table 2 is similar but the bits have shifted. In comparison with the series of Table 1, C"1 for which b"(1)-(4) are shown by "0, 1, 0, 1" has C1 shifted by one bit forward (or backward). Similarly, C"2 shown by "0, 0, 1, 1" has "1, 1, 0, 0" C2 shifted by two bits. Further similarly, C"3 shown by "0, 1, 1, 0" has "1, 0, 0, 1" C3 shifted by two bits. Here, k bit shift means k=1 for the series C"1 and k=2 for the series C"2 and C"3 when the following equation is applied by using b"(n) mentioned above, $$b"(n) = b(n+k) \quad (6).$$

In the Hadamard codes, codes of the same bit cycle group are separated by the amount of phase deviation for the same bit cycle thereof. In other words, the information for separation is contained in each code (each series) in the form of phase information. For example, both C2 and C3 belong to the bit cycle 4 group, and they are separated at the time of their detection by the phase information of C2 and C3.

In other words, this necessitates setting the same bit shift amount k bit for each bit cycle group when the above-mentioned bit shift amount is set for each series, and a new combination of code series is set. Inversely, when a different bit shift amount is set in a same bit cycle group, codes cannot be separated and therefore this cannot be executed. For example, when the bit shift amount k for C2 is set 1 and the bit shift amount k for C3 is set 0 with respect to C2="1, 1, 0, 0" and C3="1, 0, 0, 1", the new code series for both of them will be "1, 0, 0, 1" or the same series. As a result, in the process of signal processing after the light-sensitive element, these two series cannot be separated.

Let us see here the total value of adding for each bit or each point in time of the series C1, C2 and C3 and the series C"1, C"2 and C"3. According to Table 1 and Table 2, the total of the original series adds up to "3, 1, 1, 1," while the new series generated by the bit shift of bits turns up to be "0, 2, 2, 2." This can be summed up as follows from the viewpoint of the power source unit of the device;

(1) The series is constituted entirely by "2" except "0" of b(1) and the impedance fluctuation on the LD drive circuit side is small.

(2) The maximum consumption current (the peak driving current) decreased from "3" to "2."

And from the viewpoint of light-sensitive elements,

The maximum level of the light receiving signal declined relatively from "3" to "2."

With respect to the effect of these (1), (2) and (3), as a result of (1), periodical noises within the circuit are less likely to occur because fluctuation of impedance (load) is contained. As a result of (2), the only requirement for the power unit for the device is to supply the light source elements with current corresponding to "2" and therefore it is possible to reduce the power capacity required for the power unit of the device. And as the result of (3), it is enough to receive light of the range corresponding to "2," to proceed to photoelectric conversion and to signal processing for detection, and therefore the dynamic range of inputs of the light-sensitive elements and the signal processing unit can be expanded.

Then, we will verify the process of CDMA modulation and demodulation actually using the series C"1, C"2, and C"3 and the effect obtained thereby. Here, we will lump together C"1, C"2 and C"3, and call them a new Hadamard series.

Figure 7:
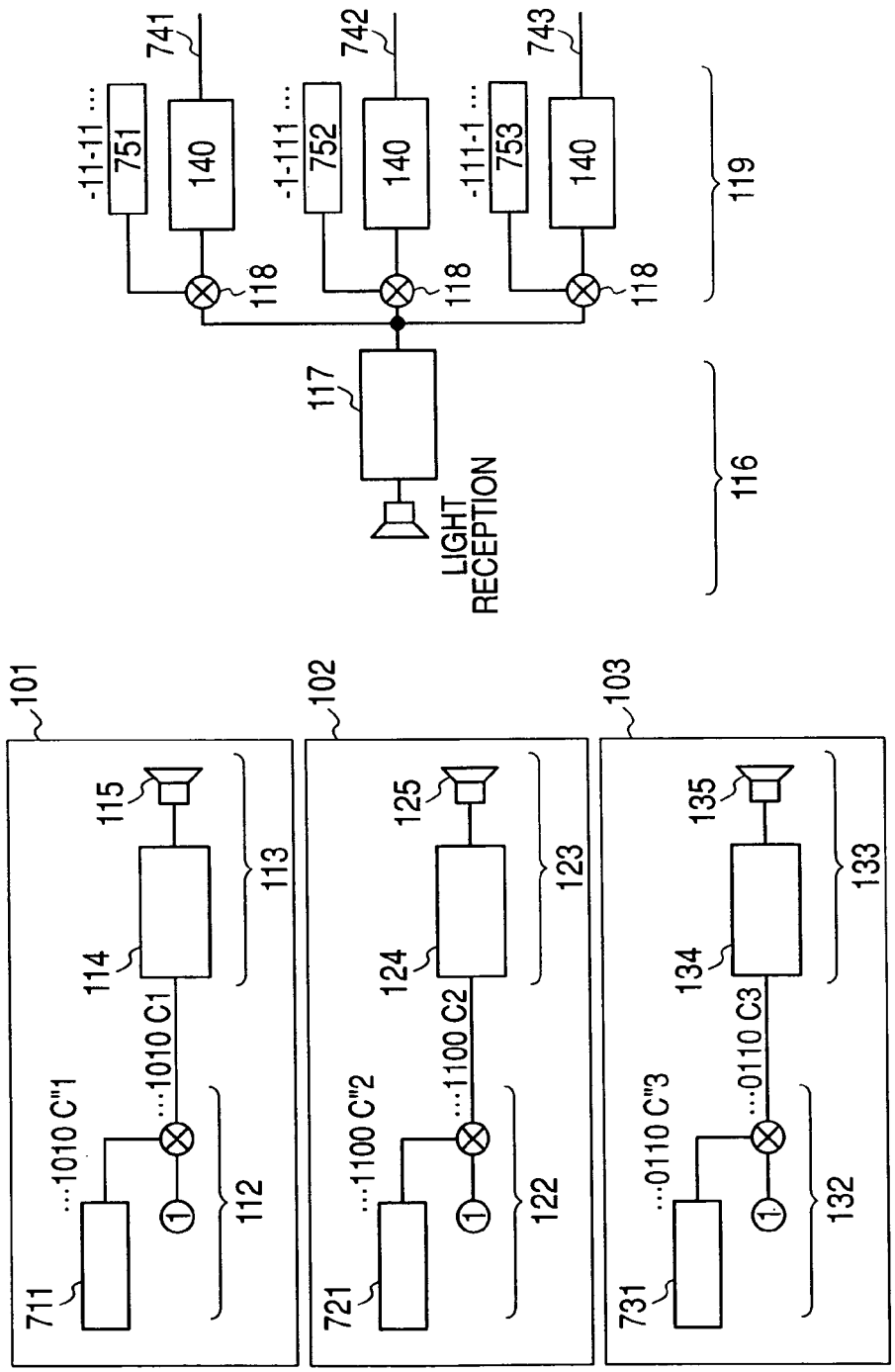
FIG. 7 is a schematic illustration of the CDMA system by the improved Hadamard codes.

FIG. 7 shows an overview of a device made by using the new Hadamard series. This corresponds to FIG. 1 used for the description of a device made by using the conventional Hadamard series. The difference with the device shown in FIG. 1 lies in that the code series generated by the code generators 711, 721 and 731 are the new Hadamard series C"1, C"2 and C"3, and that the demodulation codes generated by the demodulation code generating units 751, 752 and 753 are codes for the demodulation of the new Hadamard series. The respective correlation detecting unit 140 outputs the detection results 741, 742 and 742 in the new Hadamard series C"1, C"2 and C"3.

Figure 2:
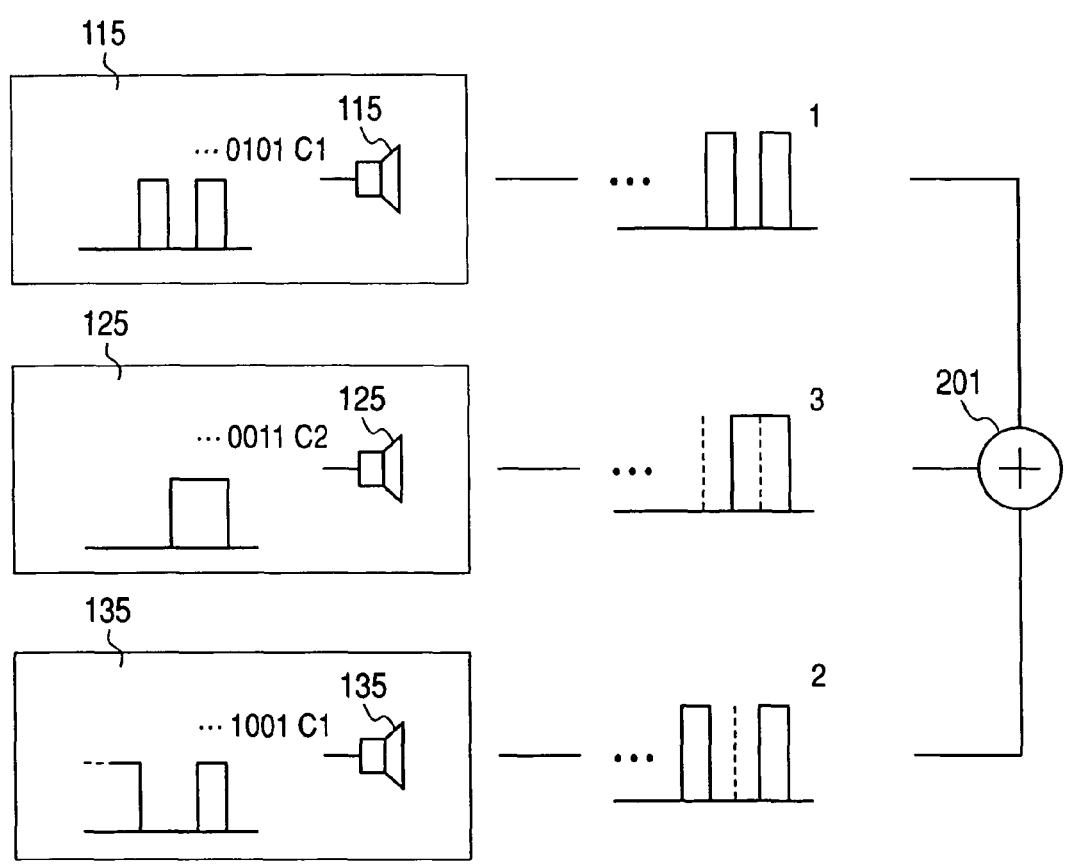
FIG. 2 is a schematic illustration showing the admixture of the driving current of the light source elements and light receiving signals.
Figure 8:
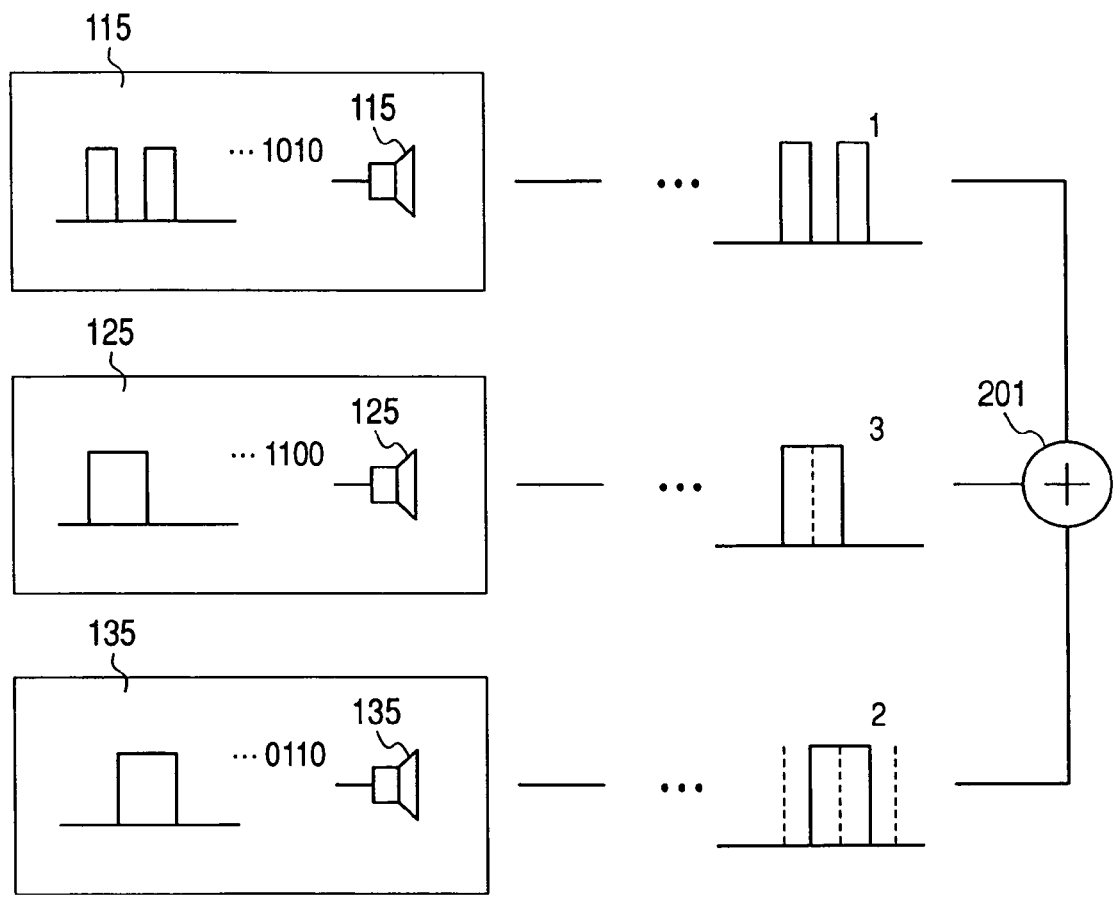
FIG. 8 is a descriptive illustration of the admixture of the driving current of light source elements and the light receiving signals by the improved Hadamard codes.
Figure 9:
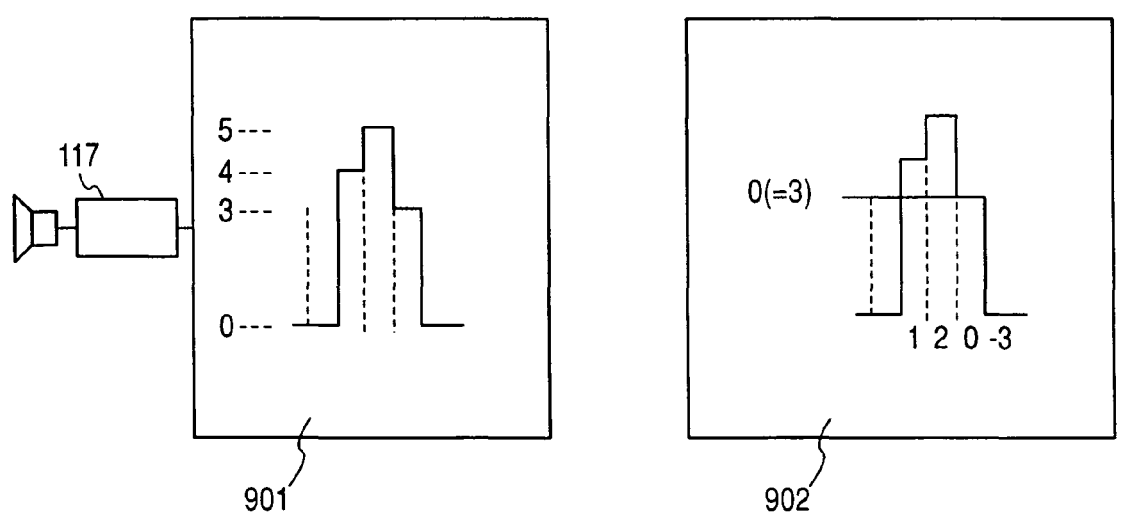
FIG. 9 is an illustration showing an example of light receiving signal by the improved Hadamard codes.

On the other hand, the outputs at the irradiation positions 115, 125 and 135 and the light receiving level by the light-sensitive elements are shown in FIG. 8. Here, various levels are the same values as "1, 3, and 2" shown in FIG. 2. FIG. 8 shows signals emitted from the light source elements, and FIG. 9 shows signals received by the light-sensitive elements. Here, the codes at each irradiation position in FIG. 8 are outputted by the sequential order from the right side of the figure, For example, in the case of irradiation position 115, they are outputted in the order of "0, 1, 0, 1."

Figure 3:
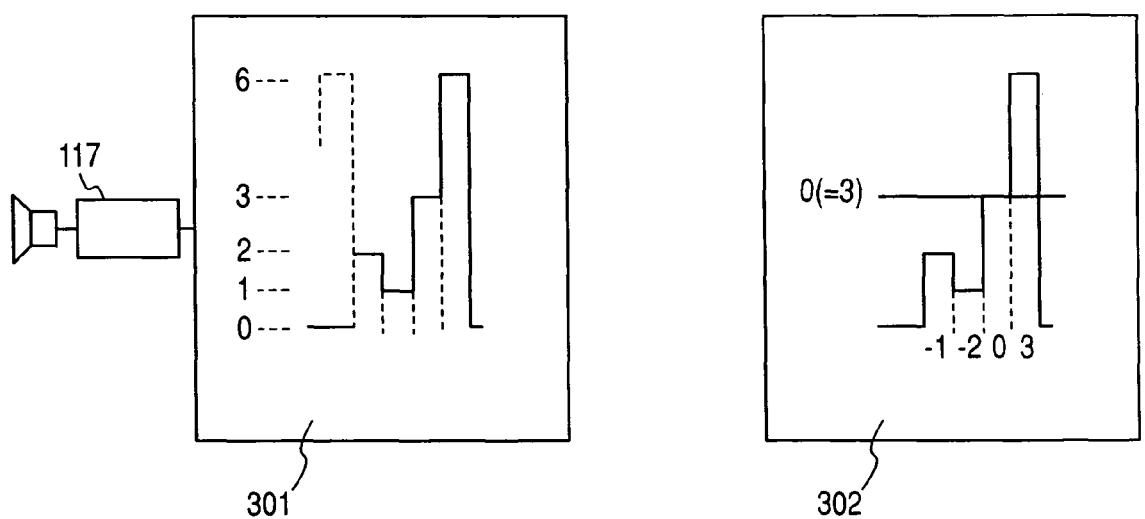
FIG. 3 is an illustration showing an example of light receiving signal by the conventional Hadamard codes.

At this time, the aggregate total of light receiving signal 901 in the case where this new Hadamard series is applied revolves in time series order of "0, 3, 5, 4." And the AC coupled light receiving signals 902 in the case where the new Hadamard series is applied revolves in the order of "−3, 0, 2, 1." When this is compared with the signals shown in FIG. 3, while the values revolve in the order "6, 3, 1, 2" in FIG. 3, in the case where the new Hadamard codes are used, the values revolve in the order of "0, 3, 5, 4," and therefore we find that:
(1) The maximum value has diminished from "6" to "5," and
(2) The average of four signals remains unchanged at "3."
As a result, we can say that the effect that we had described earlier by codes (only "1" and "0") can be realized in an actual device irrespective of individual difference in consumption current or difference in the transmission factor of light. And from (2) we can conclude that there is no change in the total amount of light, and that, with respect to white noise-type noise (dark current noise and the like), SN ratio does not deteriorate by any changes in signals.

Figure 4:
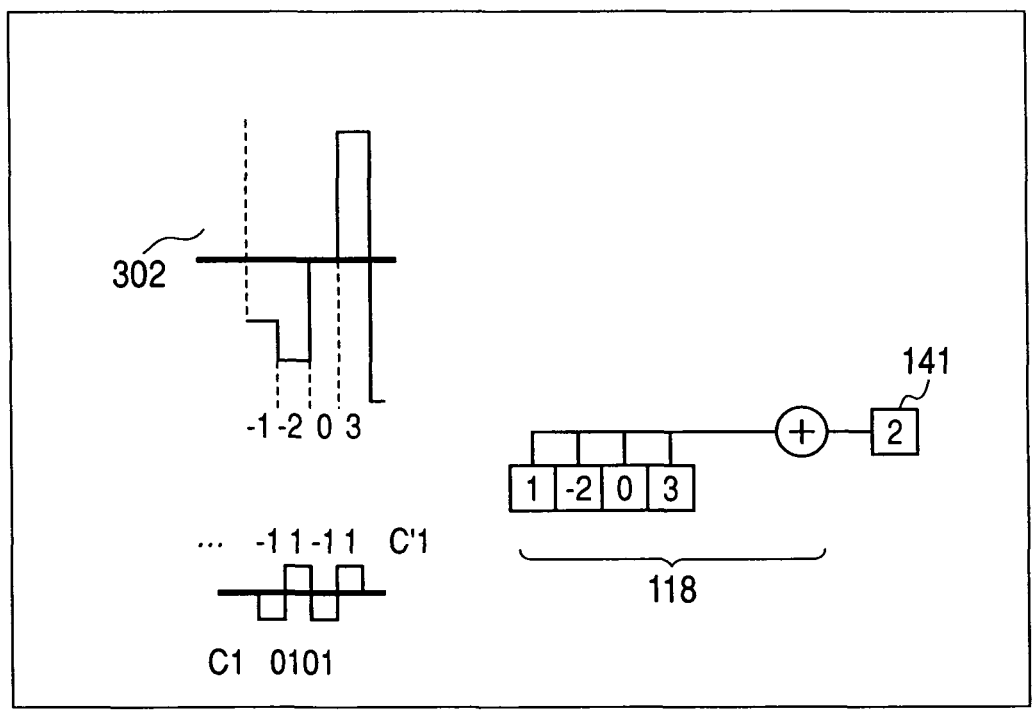
FIG. 4 is a schematic illustration showing the demodulation/detection process of a signal from the irradiation position 115.
Figure 5:
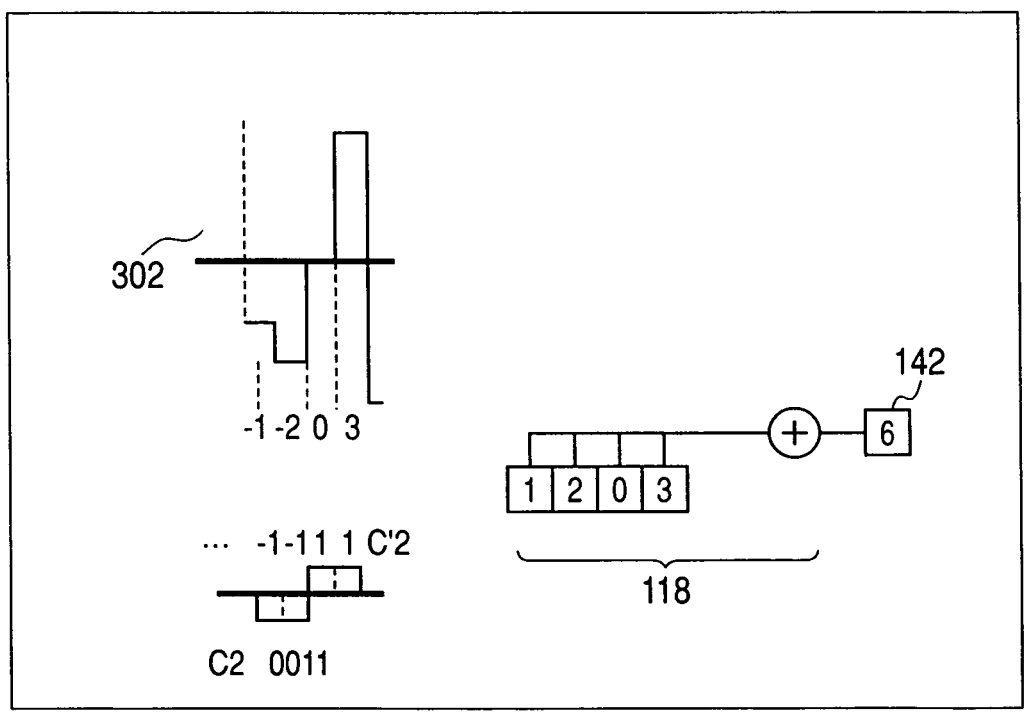
FIG. 5 is a schematic illustration showing the demodulation/detection process of a signal from the irradiation position 125.
Figure 6:
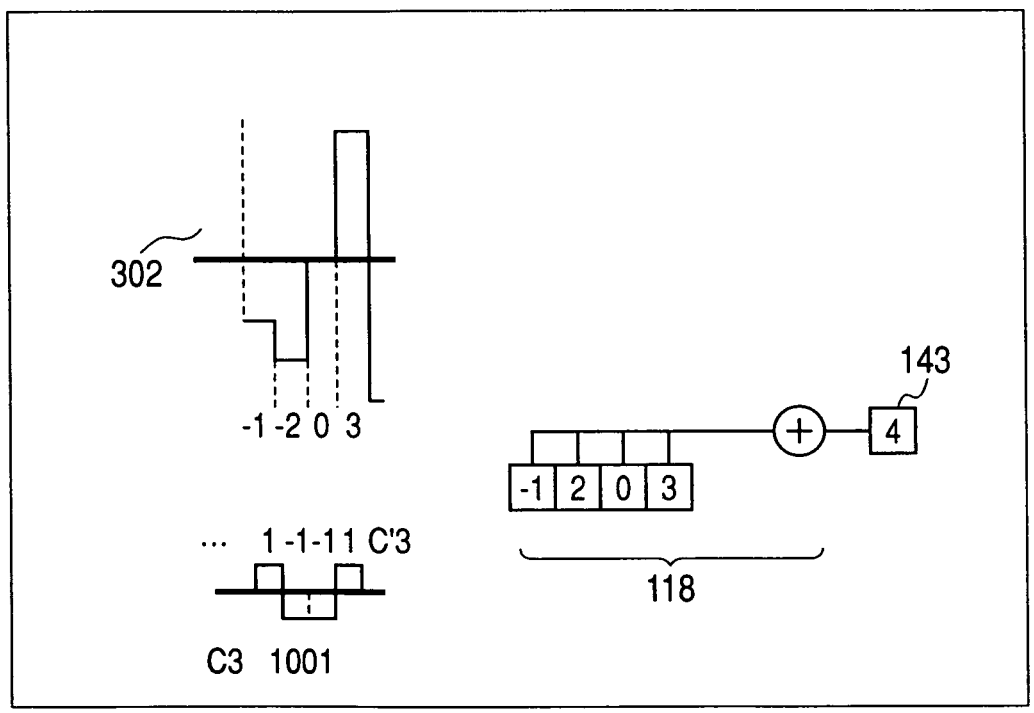
FIG. 6 is a schematic illustration showing the demodulation/detection process of a signal from the irradiation position 135.
Figure 10:
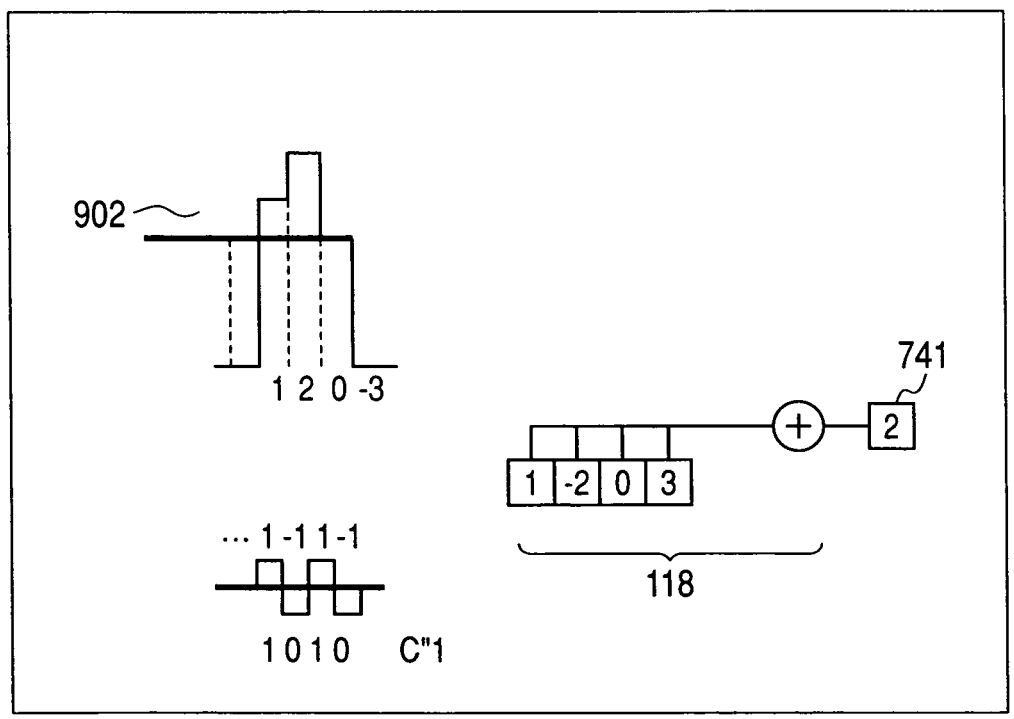
FIG. 10 is a schematic illustration showing the demodulation/detection process of the improved Hadamard code signal from the irradiation position 115.
Figure 11:
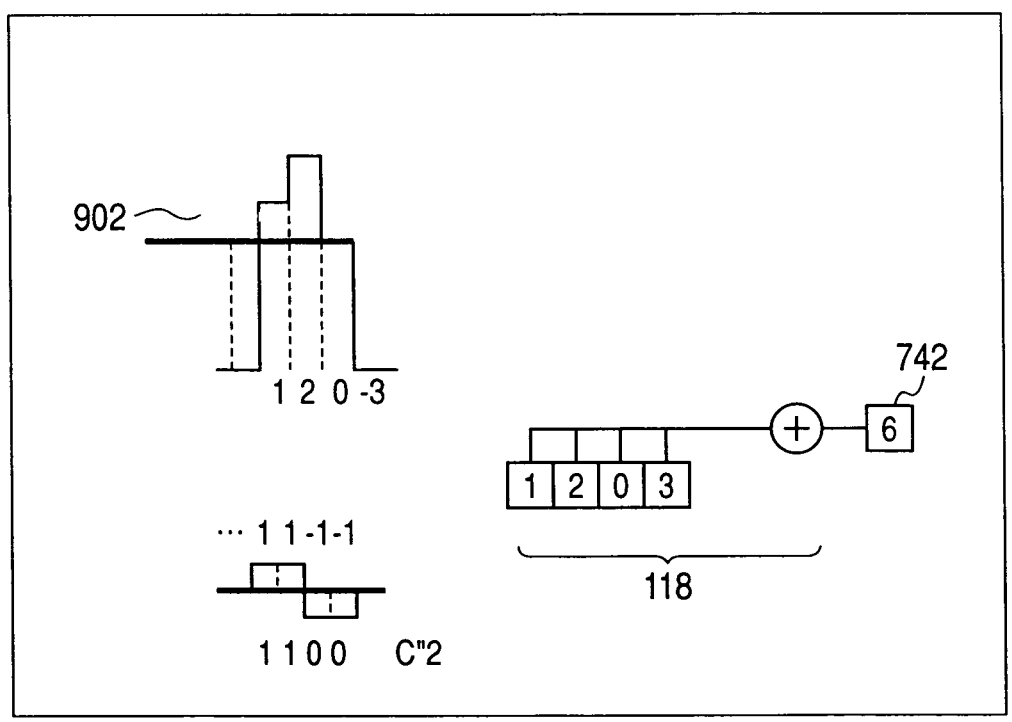
FIG. 11 is a schematic illustration showing the demodulation/detection process of the improved Hadamard code signal from the irradiation position 125.
Figure 12:
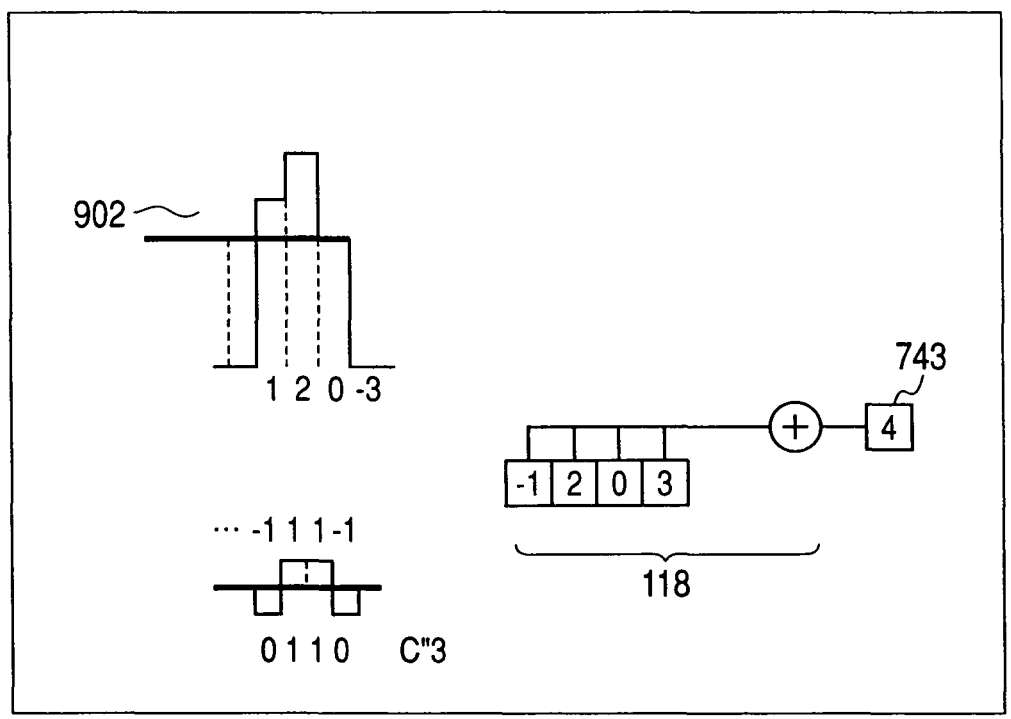
FIG. 12 is a schematic illustration showing the demodulation/detection process of the improved Hadamard code signal from the irradiation position 135.

Then, like the case in which we described the demodulation process of the conventional Hadamard series, the codes obtained by multiplying the codes of series C"1, C"2 and C"3 by 2 and subtracting 1 therefrom are respectively generated, and after multiplying the result by the value of the corresponding irradiation position, the bits of the 4 bit series are added up. This is identical to the conversion process of C1–3 and C'1–3 described above. FIG. 10, FIG. 11 and FIG. 12 show respectively the process of demodulation at the irradiation position 115, irradiation position 125 and irradiation position 135. As a result, the detected outputs are "2, 6, 4" in the corresponding order. Thus, we find that the demodulation and detection have been carried out with the same values as in the case of using the conventional Hadamard series shown in FIG. 4, FIG. 5 and FIG. 6.

So far, we have explained that it is possible to use the new Hadamard series for separating signals in an optical topography device, and that it is effective for restricting the peak value consumption current and of level of light reception. It should be noted here that the code length of the Hadamard codes is unlimited, and longer Hadamard codes can be generated by substituting recursively with the equation (1) and the equation (2), and based on this the amount of bit shift can be set for each bit length group described above. In the explanations we have made so far we have adopted series of which the bit length is 4 at the maximum, but it is possible to extend the bit length in response to the number of light sources, in other words the number of measurement points, and depending on this combination, the restriction of the peak value of consumption current and the level of light received will be more effective.

In particular, in comparison with the conventional Hadamard series, one in which the amount of bit shift is set at n/2 for the bit cycle n group which is a code length n cycle is preferable because all the initial codes are 0. For example, the C"1 mentioned above is equivalent to the series C1 of the bit cycle 2 group shifted by one bit, and the series C"2 and C"3 are equivalent to the series C2 and C2 of the bit cycle 4 groups shifted by 2 bits. Likewise, ones in which bit is shifted by n/2 for the whole bit cycle n group from longer Hadamard codes by the recursive substitution mentioned above are preferable as the new Hadamard series. These are characterized by the following features, when all the defined codes are used.
(1) The total sum of the value of the first bit turns out to be 0, and
(2) The total sum of the value of bits from the second bit to the last bit will be a predetermined value.
For example, the series of the total sum of C"1, C"2 and C"3 turns out to be "0, 2, 2, 2" as described above, and (1) the first bit is 0, and (2) the total sum of the value of the second to fourth bit turns out to be constant at 2. This arrangement is most effective for achieving the object of uniformizing load.

And the action of lighting and switching off light source elements in relation to the expression of codes is not limited to the positive logic (lighting for 1 and extinction for 0) for the form shown in Table 1. It can be a negative logic for the form shown in Table 1 (extinction for 1 and lighting for 0). Now, if the form shown in Table 1 is taken as a positive logic (extinction for 1 and lighting for 0), and if this is replaced by a negative logic (extinction for 1 and lighting for 0), the result will be C1="0, 1, 0, 1" which is the same as C"1 mentioned above. And a similar replacement will result in C2=C"2, C3=C"3. This shows that the series C"1, C"2, C"3 mentioned above is respectively an inversion of "1" and "0" of the original C1, C2 and C3. And this shows that even the negative logic expression of the original Hadamard codes can produce the smoothing effect of consumption current of light source elements and that of improving the precision of measurement mentioned above.

And even if a negative logic expression is used, it is possible to set an amount of bit shift for each bit cycle group mentioned above by the number and disposition of light sources, and to make an optimum disposition corresponding to the device.

Second Embodiment

In the first embodiment, we adopted the Hadamard codes for the code. However, with respect to M series and Gold series which are widely known PN code series other than the Hadamard codes, it is possible to generate codes by the bit shift mentioned above. For example, in the case of M series, a type of series is bit shifted and is handled as separatable code (subject to demodulation/detection). Here, the PN code is also called "pseudonoise code" and refers to the whole cyclical code wherein the code spectrum has spread out and shows a behavior close to white noise. This includes the M series. It is characterized by an outstanding self correlation. Due to this characteristic, even the same code which has gone out of timing can be separated.

In the case of M series (15 bit length) shown in Table 3, the bit cycle mentioned above is 15. Here, each bit Mb (k, n) of each series M(k) is expressed as follows:

$$Mb(k, n) = Mb(k-1, n-1) \quad (7)$$

However, in the case of k=1, k=16 is substituted on the right side, and in the case of n=1 also, n=16 is substituted. The codes C1-C15 in Table 3 express respectively 0 or 1.

will be possible by means of the method described earlier to obtain better measurement of living body than the CDMA method in which plural different M series of the same bit length are used, because the intercorrelation of different M series of the same bit length is worse than their autocorrelatilon in terms of correlation characteristic.

This is based on the use of the characteristic of the M series and the Gold series by which even the same signals which have shifted in time can be separated and erased, in other words having a high autocorrelation. And the bit length of these series is not limited to 15, and it can be 31-bit length, 63-bit length, 127-bit length, 255-bit length and so forth, and therefore can be adapted to the number of light sources of the device. If a M series or Gold series of a bit length in excess of the number of light sources is adopted, it is possible to perform the measurement of living bodies that removes the interference of light emitted by other light source elements.

This is because in a living body optical measurement device it is possible to coordinate and control action of all the light sources and detection system in the whole device and it is relatively easy to establish the synchronization among the series which is a problem in mobile communications and to supplement or maintain synchronization at the time of repair works in comparison with mobile communications.

TABLE 3

| | Time | | | | | | | | | | | | | | |
|---|---|---|---|---|---|---|---|---|---|---|---|---|---|---|---|
| | 0~t1 | t1~t2 | t2~t3 | t3~t4 | t4~t5 | t5~t6 | t6~t7 | t7~t8 | t8~t9 | t9~t10 | t10~t11 | t11~t12 | t12~t13 | t13~t14 | t14~t15 |
| | | | | | | | | bit | | | | | | | |
| Series | b(1) | b(2) | b(3) | b(4) | b(5) | b(6) | b(7) | b(8) | b(9) | b(10) | b(11) | b(12) | b(13) | b(14) | b(15) |
| Mk(1, n) | C1 | C2 | C3 | C4 | C5 | C6 | C7 | C8 | C9 | C10 | C11 | C12 | C13 | C14 | C15 |
| Mk(2, n) | C15 | C1 | C2 | C3 | C4 | C5 | C6 | C7 | C8 | C9 | C10 | C11 | C12 | C13 | C14 |
| Mk(3, n) | C14 | C15 | C1 | C2 | C3 | C4 | C5 | C6 | C7 | C8 | C9 | C10 | C11 | C12 | C13 |
| Mk(4, n) | C13 | C14 | C15 | C1 | C2 | C3 | C4 | C5 | C6 | C7 | C8 | C9 | C10 | C11 | C12 |
| Mk(5, n) | C12 | C13 | C14 | C15 | C1 | C2 | C3 | C4 | C5 | C6 | C7 | C8 | C9 | C10 | C11 |
| Mk(6, n) | C11 | C12 | C13 | C14 | C15 | C1 | C2 | C3 | C4 | C5 | C6 | C7 | C8 | C9 | C10 |
| Mk(7, n) | C10 | C11 | C12 | C13 | C14 | C15 | C1 | C2 | C3 | C4 | C5 | C6 | C7 | C8 | C9 |
| Mk(8, n) | C9 | C10 | C11 | C12 | C13 | C14 | C15 | C1 | C2 | C3 | C4 | C5 | C6 | C7 | C8 |
| Mk(9, n) | C8 | C9 | C10 | C11 | C12 | C13 | C14 | C15 | C1 | C2 | C3 | C4 | C5 | C6 | C7 |
| Mk(10, n) | C7 | C8 | C9 | C10 | C11 | C12 | C13 | C14 | C15 | C1 | C2 | C3 | C4 | C5 | C6 |
| Mk(11, n) | C6 | C7 | C8 | C9 | C10 | C11 | C12 | C13 | C14 | C15 | C1 | C2 | C3 | C4 | C5 |
| Mk(12, n) | C5 | C6 | C7 | C8 | C9 | C10 | C11 | C12 | C13 | C14 | C15 | C1 | C3 | C4 | C4 |
| Mk(13, n) | C4 | C5 | C6 | C7 | C8 | C9 | C10 | C11 | C12 | C13 | C14 | C15 | C1 | C3 | C3 |
| Mk(14, n) | C3 | C4 | C5 | C6 | C7 | C8 | C9 | C10 | C11 | C12 | C13 | C14 | C15 | C1 | C2 |
| Mk(15, n) | C2 | C3 | C4 | C5 | C6 | C7 | C8 | C9 | C10 | C11 | C12 | C13 | C14 | C15 | C1 |
| Total | 8 | 8 | 8 | 8 | 8 | 8 | 8 | 8 | 8 | 8 | 8 | 8 | 8 | 8 | 8 |

At this time, as shown in the total column, the number of light sources lighted at a time is eight. This is an inherent characteristic of the M series, because in the M series of bit cycle (bit length) a, there are (a+1)/2 "1" (lighting).

This arrangement enables to restrict the fluctuation of consumption current of light source elements when 15 light sources are used like the case wherein the Hadamard codes mentioned above are used than the case wherein plural different M series are used. When the consumption current of each light source element is constant, the range of fluctuation of consumption current by the blinking (lighting and extinction) of 15 light source elements is ideally brought to 0. This action appears in the same way when they are replaced by the Gold series. And in the case of M series, while only a few types of M series of 15 bit length can exist, by adding the process of bit shift of the codes defined in the equation (7) mentioned earlier, it becomes possible to demodulate/detect and measure the light receiving signals from the 15 light-sensitive elements in the signal processing unit. In addition, it It should be noted here that there is no restriction to the structure of the signal processing unit and the code generating unit shown in FIG. 1. Due to the progress of circuitry technology, the use of a digital code processing system is appropriate. A digital code processing system can be constituted by component parts wherein a processor called DSP, CPU or MPU is used depending on the amount of processing, the amount of computing in the pre/post process in the device and the output method of measurement result in addition to programmable logic devices such as FPGA, PLD and the like. Of course, it is possible to constitute a digital code processing system by using electronic equipment such as a general-purpose personal computer (PC), a data logger excluding or including AD, DA converting unit, and to measure and detect the result of measurement by processing codes. In addition, it is also possible to combine the structure mentioned above, to perform multiplication and the like by equipment, and to perform the whole postprocess including two-dimensional display of the detection results and statistical processing by a PC.

And there is no restriction on the mode of using devices either, and it is possible to miniaturize the power source unit of devices including batteries by taking advantage of smoothing (reduction of current peak value) effect of consumption current of the whole light source elements, and to turn them into not only stationary device but also to portable devices that can be carried. In this case, it will be possible to measure living body activities lasting over a long period of time without restricting various activities, for example various exercises of the subject of measurement and without restricting the subject of measurement, and to allow a latitude to the state or activities of the subject of measurement at the time of measurement.

Figure 13:
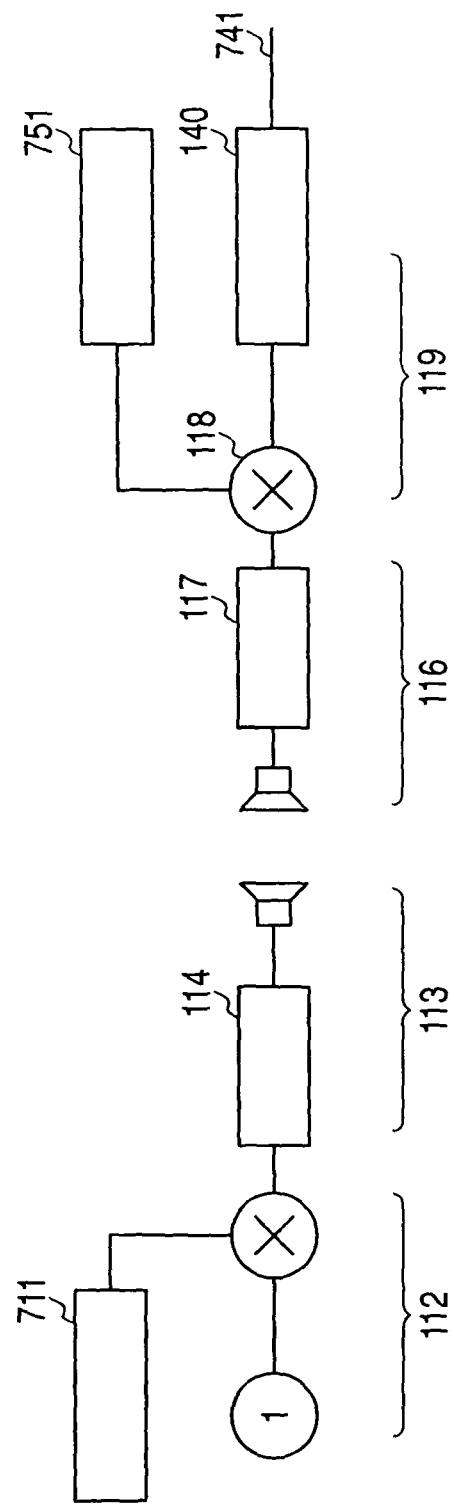
FIG. 13 is an illustration showing an example of the configuration of a CDMA system not using carrier wave.
Figure 14:
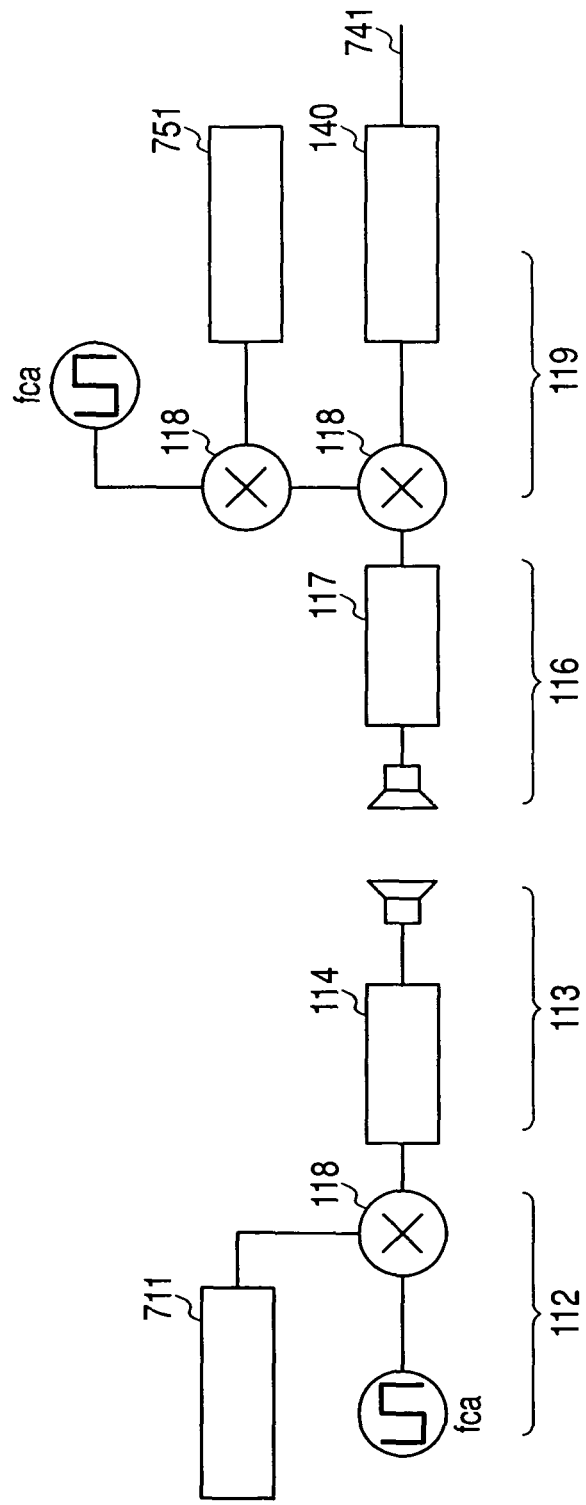
FIG. 14 is an illustration showing an example of the configuration of a CDMA system using carrier wave.
Figure 15:
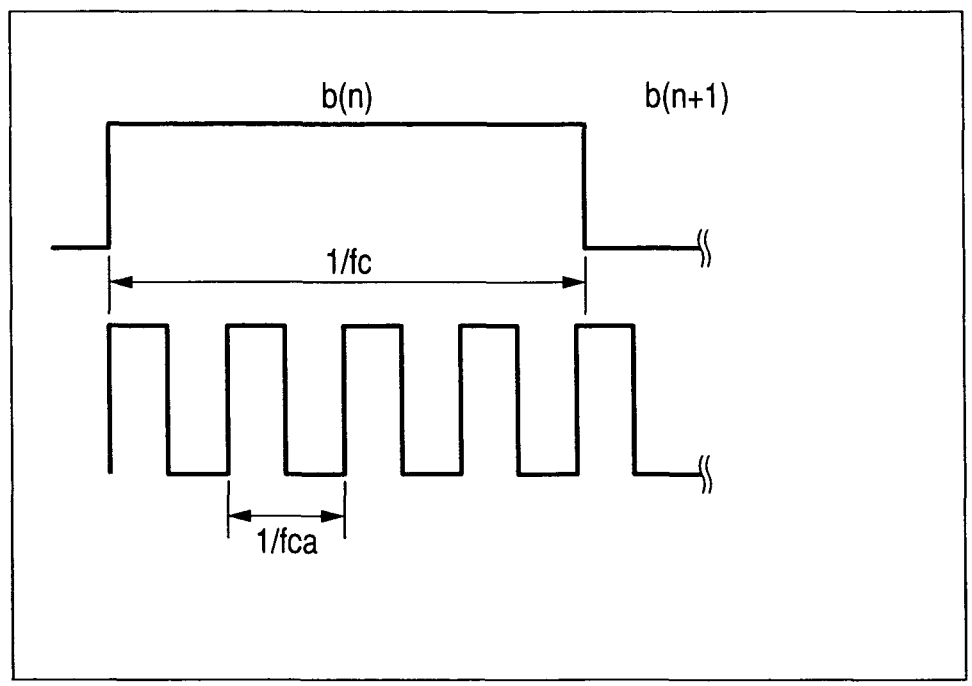
FIG. 15 is an illustration showing an example of relationship between carrier wave and chip rate.

And the signal (carrier wave) diffused by code (spread code) may not be a DC signal of a predetermined value as shown in FIG. 13. It may be, for example, a code with a rectangular wave as shown in FIG. 14. At this time, the carrier wave frequency fca is an integral multiple, in particular two power multiple of the chip speed which is the spread speed of the spread code, and it is preferable that the spread code is synchronized with the carrier wave. This is because the duty per cycle of each series turns out to be 50%, and it becomes relatively easy to simplify the internal processing of the device based on the carrier wave frequency fca. FIG. 15 shows an example thereof. In the case of the example of FIG. 15, one code b(n) of the series corresponds to four cycles of the rectangular wave of the carrier wave, wherein the equation of $fca=2^2 \times fc$ is valid.

Here, if the relationship described above is valid for fc and fca, frequency and frequency ratio are not limited. They are determined depending on the processing capacity of the device or the output interval specification of measurement results.

And among the multiplier circuits shown in FIG. 14, the unit for multiplying the carrier wave fca and the code series C'1 and the unit for multiplying the carrier wave fca and the demodulation code need not actually carry out the multiplication operation as the optical demodulating unit 112, 122, 113 and the code processing unit 119 shown in FIG. 7. It may take the method of reproducing/generating the code resulting from multiplications performed in advance by various types of memory circuits or logic circuits. It is possible to constitute freely by adapting with other parts. For example, when a memory circuit is used, it is possible to record the result of multiplication of a code series and a carrier wave as the details of recording in a memory, to read successively the details of recording by the control clock code at the time of living body measurement and to output the same as the multiplication result, and this is preferable from the viewpoint of simplifying circuits and reducing the amount of processing.

Figure 16:
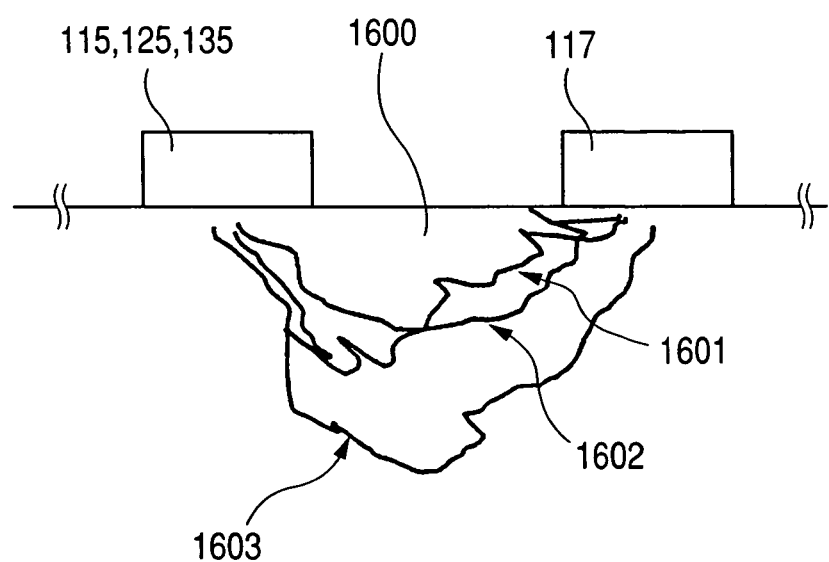
FIG. 16 is a conceptual illustration of the transmission of light by three light source elements.

The above description has been based on the CDMA method used to separate codes mutually between spatial positions (spatial separation) at which the subject of measurement is irradiated with the emitted light called irradiation positions. The application of the CDMA method is not limited to this and it can be applied equally to the mutual separation among the different wavelengths of emitted light (wavelength separation). For example, as shown in FIG. 16, it is preferable to irradiate the subject with emitted light with different wavelength 1601, 1602 and 1603 from the same irradiation position to measure the same object point of measurement of the living body. This is because it is possible to measure the same point of the subject chosen as the object of measurement with light of different wavelength. Furthermore, it is more preferable to execute precise measurements over an extensive scope by implementing various measurements at the same time by combining the spatial separation and wavelength separation mentioned above by setting plural positions of multi-wavelength irradiation mentioned above.

Figure 17:
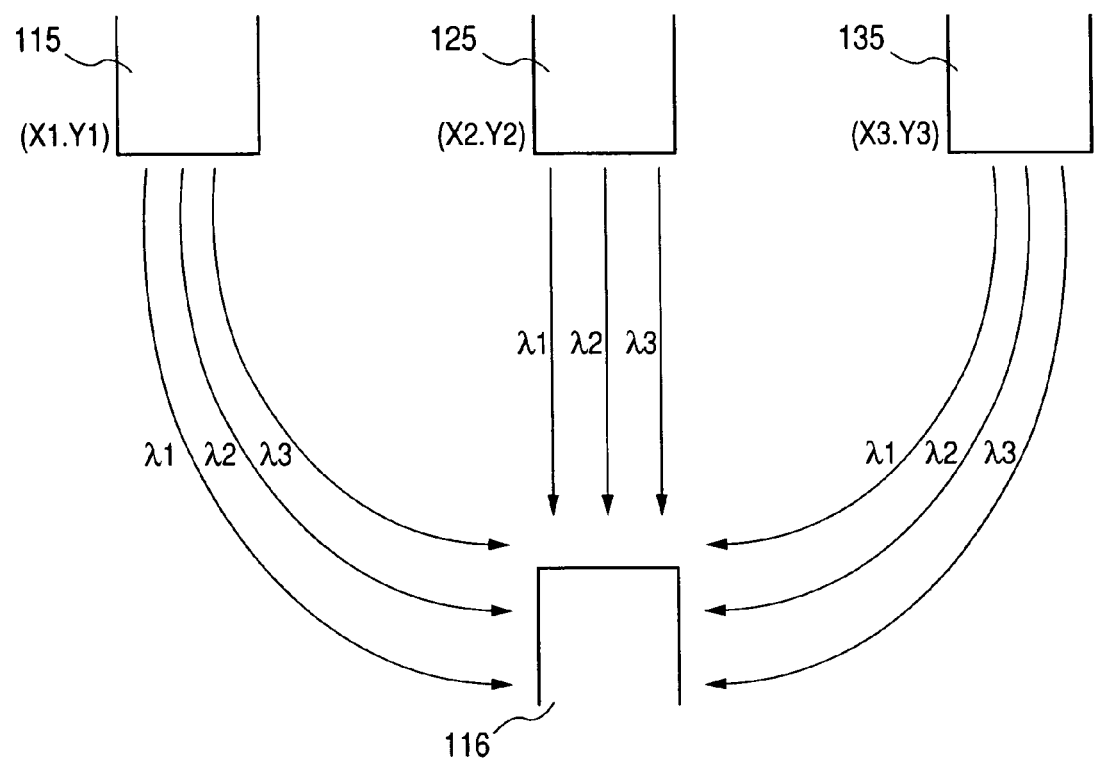
FIG. 17 is a conceptual illustration of the transmission of light by three light source elements with three wavelengths.
Figure 18:
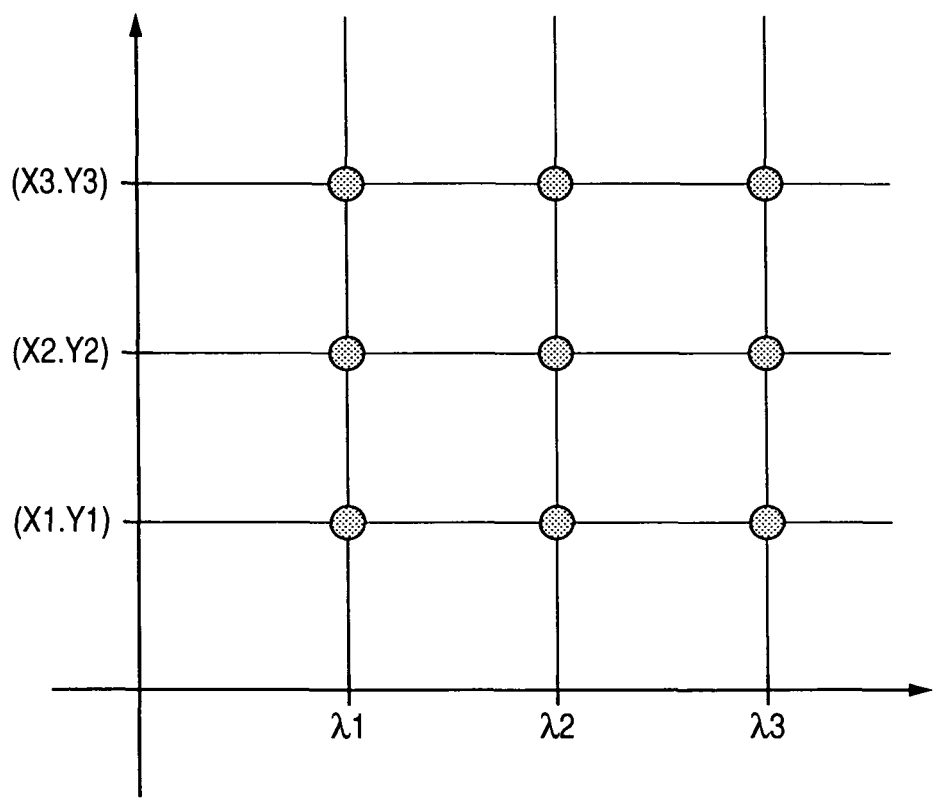
FIG. 18 is an illustration showing the concept of transmission and separation of light by three light source elements with three wavelengths.

For example, FIG. 17 shows the case of measuring by transmitting light respectively with three wavelengths to a light detecting unit 116 from three irradiation positions 115, 125 and 135 set on the same plane (XY plane) in the X axis direction. If the codes (CDMA codes) for performing intensity modulation of each light in this case are different, it will be possible to perform spatial separation and wavelength separation at the same time. In this case, the concept of separation by codes is as shown in FIG. 18, and it will be possible to separate nine types of codes by three different wavelengths ($\lambda 1, \lambda 2, \lambda 3$) at three different irradiation positions ($x1 \neq x2 \neq x3, y1 \neq y2 \neq y3$). In FIG. 18, the vertical axis shows the separation of irradiation positions, or spatial separation, and the horizontal axis shows the wavelength separation by three wavelengths ($\lambda 1, \lambda 2, \lambda 3$). Here, the code for each optical signal must be different. And for the purpose of explanation, the value in the z axis direction is considered to be same, and we explained only on the xy plane. However, three-dimensional shape such as human body whose value in the x axis direction is different may be chosen as the object of measurement.

And in separating codes, if light emitted from separate light sources does not reach the same light-sensitive element because of distance or the transmission factor of the object of measurement, it is possible to use the same code for different light source (irradiation position). However, in this case it is necessary to confirm that actually emitted light of the same code does not reach the same light-sensitive element and no code interference/wrong measurement occurs.

Figure 19:
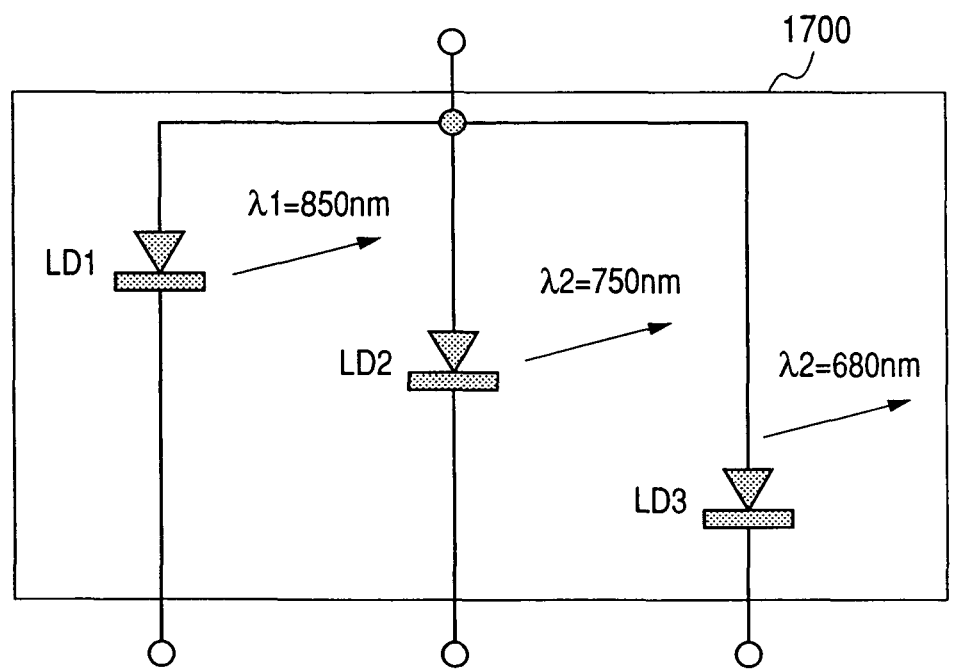
FIG. 19 is an illustration showing an example of the structure of a three wavelength LD.

And if the same irradiation position is chosen, it is possible to mount three light source elements in one same package and use light sources with three emitted light output. A light source 1700 with three emitted light output is shown in FIG. 19. This light source outputs emitted light of respectively different wavelengths $\lambda 1, \lambda 2, \lambda 3$ from light source elements LD1, LD2, and LD3 and irradiate light from almost the same point. And as for the method of irradiating light from three light source elements on the same point or as close as possible thereto, the method of mixing the emitted light from various light source elements by optical elements such as WDM and the like and irradiating the same point therewith may be used.

As for $\lambda 1, \lambda 2, \lambda 3$, there is no restrictions for the constitution of device, and it is possible to select and/or set (the wavelength value) depending on the object of measurement or the feasibility of producing light-source element. In the case of the light source 1700 having three emitted light outputs shown in FIG. 19, the amount of oxygenated and deoxygenated hemoglobin contained in the blood are measured in measuring blood bodies in motion, and in this connection for $\lambda 1, \lambda 2, \lambda 3$ for example, the values of 850 nm, 750 nm and 680 nm are chosen. However, if for example water (body fluid) is chosen for the object of measurement, it is possible to change to a wavelength suitable for this.

As for light emitting method/element, it is possible to use LD (laser diode), VCSEL element, LED element, RCLED element and other light source elements. And the methods of irradiating the irradiation position are unlimited, and for example the method of making the light output terminal of light source element get into contact directly with the irradiation position, and the method of transmitting/irradiating the emitted light of the light source element isolated from the irradiation position to the irradiation position through an optical fiber can be implemented.

The light source elements LD1, LD2 and LD3 shown in FIG. 19 have respectively common anodes. However, the light source elements are not limited to this construction. It is possible to make the cathode common in response to the driving circuit of the light source element, to contain an mPD (monitor photodiode) for measuring the optical output of the light source element, and it is also possible to measure the living body activities by using light-sensitive elements and at the same time to monitor the optical output of the light source elements and to monitor for their control. In this case, there is no limit to the connection with the mPD, and for example the anode of the light source elements LD1, LD2 and LD3 shown in FIG. 19 and the cathode of the mPD may be connected in common, and to make the anode and cathode of the mPD and the anode and cathode of the light source elements LD1, LD2 and LD3 independent. Moreover, there is no limit to the number of built-in mPDs, and it is possible to monitor the emitted light from the light source elements LD1, LD2 and LD3 with a single mPD and to monitor emitted light separately by three mPDs, In case of monitoring three emitted light by a single mPD, it will be necessary to demodulate/detect the signal level (light emitting level) by the signal processing similar to the light-sensitive elements described above and thereafter.

As for the specific method of monitoring for measuring or controlling optical output, it is possible to use the method of independently measuring and monitoring by using light-sensitive elements by time series at the time of measurement, and subtracting the respective measurement result immediately or after the completion of the measurement as a post-process, or the APC (auto power control) method wherein the measurement result of code level by a mPD is considered as the light emitting level by the light source elements and the amplitude of the driving current of the light source elements is controlled so that the measurement result of the code level by this mPD may be constant. In the case of processing by subtracting two types of measurement results, changes in time series of the transport factor (rate of transmission decrease) between light source elements and light-sensitive elements can be calculated by the subtraction mentioned above, and the APC control enables to measure changes in time series of the level of light received after the demodulation/detection by the light-sensitive elements as the changes in time series of the rate of transmission decrease.

And there is absolutely no limit to light-sensitive elements with respect to their system and materials. For example, it is possible to choose and use not only SIPD (silicon photodiode), but also APD (avalanche photodiode), PMT (photomultiplier tube) and other light-sensitive elements depending on the purpose, intensity of received light signals, light emitting wavelength and the like. In addition, with respect to materials, it is possible to choose and use known light-sensitive elements constituted by various semiconductors and various chemical compounds including the same.

Figure 20:
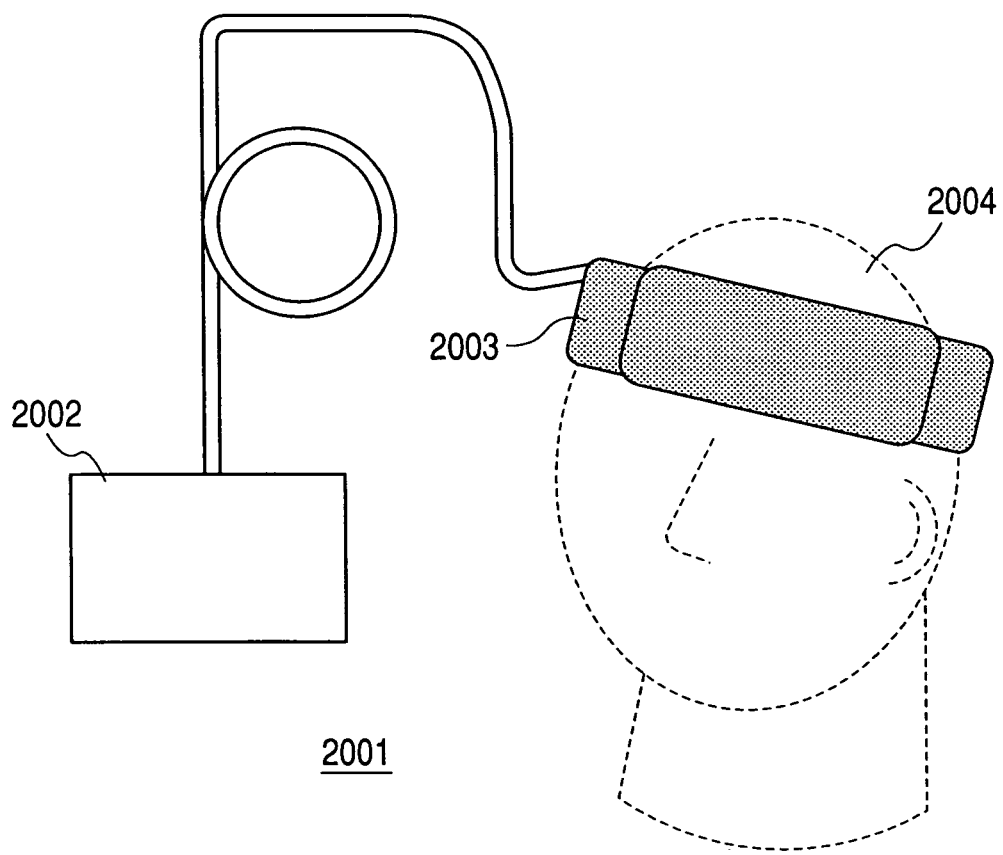
FIG. 20 is an illustration showing an example of living body optical measurement system.

An embodiment of (living body optical measurement) device 2001 made by combining the methods described above is shown in FIG. 20. This device is constituted by the main unit 2002 including a PC and a probe unit 2003. The main unit 2002 sets and controls measurements in general, records and stores, and display the results thereof. The probe unit 2003 is fixed on the head of the subject 2004, and irradiates light on the head of the subject 2004 and detects data therefrom. The modulation of light intensity and the demodulation of the light receiving signal by the CDMA codes of the present invention are performed by the main unit 2002. However, it is possible to make the probe unit 2003 perform these functions by the design of the circuit.

This device 2001 has the functions of measuring, displaying and recording changes in the brain activity of the subject by measuring blood volume/hemodynamics of oxygenated hemoglobin (OxHb) and deoxygenated hemoglobin (DeOxHb) in the brain. The main unit 2002 can set light intensity of the irradiation signal and demodulation code for each irradiation position and controls the beginning and end of the irradiation and measurement of light signals. And based on the data obtained by measurement, it has functions of displaying changes in light received in the time axis direction and time fluctuations of blood volume/hemodynamics of OxHb, DeOxHb calculated according to the same, and changes in blood volume/hemodynamics of OxHb, DeOxHb in each region of the brain resulting from the same, and recording the data in the attached auxiliary recording device (HDD, CD-ROM, MO and the like). It has also the function of processing statistically the measurement data, and recording the results in the auxiliary recording device. According to the present invention, the power source of the main unit 2002 can be reduced smaller in capacity and the precision of measurement can be improved while the dimension of device is reduced.

The present invention provides a device with small fluctuations in power load by adopting a living body optical measurement device using the conventional CDMA system. This contributes to the miniaturization of device and enables to improve the precision of measurement at the same time. The miniaturization of device reduces the restriction on the subject of measurement, and the device can be used in a wide area including specialized institutions such as medical, welfare, research institutions, sport, amusement, education and the like.

What is claimed is:

1. A living body optical measurement system, comprising:
a plurality of light irradiating units each respectively including a code generating unit configured to generate a distinct modulation code from a plurality of modulation codes that are based on Hadamard codes, a modulating unit for generating an intensity modulated signal modulated by the distinct modulation code generated by the code generating unit of the light irradiating unit, and a light source blinking according to the intensity modulated signal supplied from the modulating unit of the light irradiating unit;
a light detecting unit for detecting light that is transmitted through a living body irradiated with the light sources contained in the plurality of light irradiating units and outputting an electric signal; and
a signal processing unit for computing correlations between the electric signal output by the light detecting unit and a plurality of modulation codes that are respectively equivalent to the distinct modulation codes generated by the respective modulating units of the plurality of light irradiating units, and
wherein each of the plurality of modulation codes has a distinct bit sequence that is shifted from an original bit sequence of a corresponding Hadamard code by n/2 bits, where 'n' is a bit cycle of the original bit sequence of the corresponding Hadamard code for the modulation code.

2. The living body optical measurement system according to claim 1, wherein a correlation between the Hadamard codes and the modulation codes is a negative logic.

3. The living body optical measurement system according to claim 1, wherein each light irradiating unit comprises a plurality of light sources for respectively emitting light with a different wavelength.

4. The living body optical measurement system according to claim 1, wherein the distinct bit sequence of each of the plurality of modulation codes is shifted from the original bit sequence of the corresponding Hadamard code to restrict a peak value of consumption current and a peak value of level of light reception.

\* \* \* \* \*